(12) United States Patent
Pilpel et al.

(10) Patent No.: US 9,814,799 B2
(45) Date of Patent: Nov. 14, 2017

(54) ONE COMPONENT FIBRIN GLUE COMPRISING A POLYMERIZATION INHIBITOR

(71) Applicant: Omrix Biopharmaceuticals Ltd., Rehovot (IL)

(72) Inventors: Yair Pilpel, Rehovot (IL); Ashley Deanglis, Skillman, NJ (US); Yuri Zherdev, Rehovot (IL); Sivan Doron, Moshav Arugot (IL); Israel Nur, Moshav Timmorim (IL)

(73) Assignees: Omrix Biopharmaceuticals Ltd., Rehovot (IL); Ethicon, Inc., Somerville, NJ (US)

(*) Notice: Subject to any disclaimer, the term of this patent is extended or adjusted under 35 U.S.C. 154(b) by 14 days.

(21) Appl. No.: 14/560,329

(22) Filed: Dec. 4, 2014

(65) Prior Publication Data

US 2015/0174289 A1 Jun. 25, 2015

Related U.S. Application Data

(60) Provisional application No. 61/920,646, filed on Dec. 24, 2013.

(30) Foreign Application Priority Data

Dec. 24, 2013 (IL) .......................................... 230151

(51) Int. Cl.
*A61L 24/00* (2006.01)
*A61L 24/10* (2006.01)

(52) U.S. Cl.
CPC ......... *A61L 24/001* (2013.01); *A61L 24/0015* (2013.01); *A61L 24/106* (2013.01); *A61L 24/108* (2013.01); *A61L 2300/25* (2013.01); *A61L 2300/434* (2013.01); *A61L 2400/06* (2013.01)

(58) Field of Classification Search
None
See application file for complete search history.

(56) References Cited

U.S. PATENT DOCUMENTS

| | | | |
|---|---|---|---|
| 5,219,328 A | 6/1993 | Morse et al. | |
| 5,318,524 A | 6/1994 | Morse et al. | |
| 5,478,810 A | 12/1995 | Stuber et al. | |
| 5,607,858 A | 3/1997 | Stuber et al. | |
| 5,723,579 A | 3/1998 | Buettner et al. | |
| 5,750,657 A | 5/1998 | Edwardson et al. | |
| 5,792,835 A | 8/1998 | Tse et al. | |
| 5,831,005 A | 11/1998 | Zuckerman et al. | |
| 5,877,278 A | 3/1999 | Zuckerman et al. | |
| 5,977,301 A | 11/1999 | Zuckerman et al. | |
| 5,985,315 A * | 11/1999 | Patat | A61L 24/106 424/443 |
| 6,121,232 A | 9/2000 | Nur et al. | |
| 6,262,236 B1 | 7/2001 | Edwardson et al. | |
| 6,268,483 B1 | 7/2001 | Edwardson et al. | |
| 6,500,427 B1 | 12/2002 | Heimburger et al. | |
| 6,908,899 B2 | 6/2005 | Smith | |
| 7,125,569 B2 | 10/2006 | Nur et al. | |
| 8,367,802 B2 | 2/2013 | Falus et al. | |
| 8,513,380 B2 | 8/2013 | Barker | |
| 2010/0249044 A1* | 9/2010 | Walker | A61L 24/106 514/21.2 |
| 2013/0149292 A1 | 6/2013 | Chtourou | |

FOREIGN PATENT DOCUMENTS

| | | |
|---|---|---|
| EP | 0592242 | 7/2003 |
| EP | 1390485 | 10/2006 |
| WO | WO 93/05822 | 4/1993 |
| WO | WO 98/20931 | 5/1998 |
| WO | WO 98/33533 | 8/1998 |
| WO | WO 02/095019 | 11/2002 |

OTHER PUBLICATIONS

Dickneite, G. et al. 'A comparison of fibrin sealants in relation to their in vitro and in vivo properties' Thrombosis Res (2003) vol. 112 pp. 73-82.
Laudano, A.P. et al 'Synthetic peptide derivatives that bind to fibrinogen and prevent the polymerization of fibrin monomers' PNAS (1978) vol. 75, No. 7 pp. 3085-3089.
Nguyen, J.T. et al 'Improving SH3 domain ligand selectivity using a non-natural scaffold' Chem Biol. (2000) vol. 7, No. 7 pp. 463-473.
Raccuia, J.S. et al. 'Comparative Efficacy of Topical Hemostatic Agents in a Rat Kidney Model' Am J Surg. (1992) vol. 163, No. 2 pp. 234-238.
Simon, R.J. et al. 'Peptoids: A modular approach to drug discovery' Proc. Natl. Acad. Sci. USA (1992) vol. 89, No. 2 pp. 9367-9371.
Tabélé, C. et al. 'Organic Glues or Fibrin Glues from Pooled Plasma: Efficacy, Safety and Potential as Scaffold Delivery Systems' J Pharm Pharmaceut Sci (2012) vol. 15, No. 1 pp. 124-140.
Stabenfeldt et al 'Engineering fibrin polymers through engagement of alternative polymerization mechanisms' Biomaterials, vol. 33, No. 2 (2011) pp. 535-544.
International Preliminary Report on Patentability re: PCT/IL2014/000063 dated Jun. 28, 2016.
Stuart and Young (1984), "Solid Phase Peptide Synthesis," Solid Phase Peptide Synthesis, Methods Enzymol., Second Edition, (Continued)

*Primary Examiner* — Michelle F Paguio Frising
(74) *Attorney, Agent, or Firm* — David R. Crichton

(57) ABSTRACT

Provided herein are stable liquid sealant formulations comprising fibrin monomers and a reversible fibrin polymerization blocking agent, methods of preparing and using the formulations.

14 Claims, 2 Drawing Sheets

(56) References Cited

OTHER PUBLICATIONS

Pierce Chemical Company, 289, Academic Press, Inc., NY (1997).
International Search Report re: PCT/IL2014/000063 dated Apr. 13, 2015.

* cited by examiner

SEQUENCE LISTING

<160> NUMBER OF SEQ ID NOS: 42

<210> SEQ ID NO 1
<211> LENGTH: 4
<212> TYPE: PRT
<213> ORGANISM: ARTIFICIAL
<220> FEATURE:
<223> OTHER INFORMATION: Synthetic peptide

<400> SEQUENCE: 1

Gly Pro Arg Pro
1

<210> SEQ ID NO 2
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 2

Gly Pro Arg Pro Pro
1               5

<210> SEQ ID NO 3
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 3

Gly Pro Arg Pro Ala
1               5

<210> SEQ ID NO 4
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 4

Gly Pro Arg Pro Ser
1               5

<210> SEQ ID NO 5
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 5

Gly Pro Arg Pro Lys
1               5

<210> SEQ ID NO 6
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 6

Gly Pro Arg Pro Phe
1               5

```
<210> SEQ ID NO 7
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 7

Gly Pro Arg Pro Gly
1               5

<210> SEQ ID NO 8
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 8

Gly Pro Arg Pro Trp
1               5

<210> SEQ ID NO 9
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 9

Gly Pro Arg Pro Tyr
1               5

<210> SEQ ID NO 10
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 10

Gly Pro Arg Pro Val
1               5

<210> SEQ ID NO 11
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 11

Gly Pro Arg Pro Ile
1               5

<210> SEQ ID NO 12
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 12

Gly Pro Arg Pro Asp
1               5
```

```
<210> SEQ ID NO 13
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 13

Gly Pro Arg Pro Glu
1               5

<210> SEQ ID NO 14
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 14

Gly Pro Arg Pro Gly
1               5

<210> SEQ ID NO 15
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 15

Gly Pro Arg Pro Ser
1               5

<210> SEQ ID NO 16
<211> LENGTH: 6
<212> TYPE: PRT
<213> ORGANISM: ARTIFICIAL
<220> FEATURE:
<223> OTHER INFORMATION: Synthetic peptide

<400> SEQUENCE: 16

Gly Pro Arg Pro Pro Pro
1               5

<210> SEQ ID NO 17
<211> LENGTH: 6
<212> TYPE: PRT
<213> ORGANISM: ARTIFICIAL
<220> FEATURE:
<223> OTHER INFORMATION: Synthetic peptide

<400> SEQUENCE: 17

Gly Pro Arg Pro Gly Gly
1               5

<210> SEQ ID NO 18
<211> LENGTH: 6
<212> TYPE: PRT
<213> ORGANISM: ARTIFICIAL
<220> FEATURE:
<223> OTHER INFORMATION: Synthetic peptide

<400> SEQUENCE: 18

Gly Pro Arg Pro Pro Arg
1               5
```

```
<210> SEQ ID NO 19
<211> LENGTH: 6
<212> TYPE: PRT
<213> ORGANISM: ARTIFICIAL
<220> FEATURE:
<223> OTHER INFORMATION: Synthetic peptide

<400> SEQUENCE: 19

Gly Pro Arg Pro Arg Pro
1               5

<210> SEQ ID NO 20
<211> LENGTH: 6
<212> TYPE: PRT
<213> ORGANISM: ARTIFICIAL
<220> FEATURE:
<223> OTHER INFORMATION: Synthetic peptide

<400> SEQUENCE: 20

Gly Pro Arg Pro Ala Gly
1               5

<210> SEQ ID NO 21
<211> LENGTH: 6
<212> TYPE: PRT
<213> ORGANISM: ARTIFICIAL
<220> FEATURE:
<223> OTHER INFORMATION: Synthetic peptide

<400> SEQUENCE: 21

Gly Pro Arg Pro Gly Gly
1               5

<210> SEQ ID NO 22
<211> LENGTH: 5
<212> TYPE: PRT
<213> ORGANISM: ARTIFICIAL
<220> FEATURE:
<223> OTHER INFORMATION: Synthetic peptide

<400> SEQUENCE: 22

Gly Lys Arg Pro Gly
1               5

<210> SEQ ID NO 23
<211> LENGTH: 4
<212> TYPE: PRT
<213> ORGANISM: ARTIFICIAL
<220> FEATURE:
<223> OTHER INFORMATION: Synthetic peptide

<400> SEQUENCE: 23

Gly Lys Arg Val
1

<210> SEQ ID NO 24
<211> LENGTH: 4
<212> TYPE: PRT
<213> ORGANISM: ARTIFICIAL
<220> FEATURE:
<223> OTHER INFORMATION: Synthetic peptide

<400> SEQUENCE: 24

Gly His Arg Pro
1

<210> SEQ ID NO 25
```

```
<211> LENGTH: 7
<212> TYPE: PRT
<213> ORGANISM: ARTIFICIAL
<220> FEATURE:
<223> OTHER INFORMATION: Synthetic peptide

<400> SEQUENCE: 25

Gly Pro Arg Pro Ala Ala Cys
1               5

<210> SEQ ID NO 26
<211> LENGTH: 8
<212> TYPE: PRT
<213> ORGANISM: ARTIFICIAL
<220> FEATURE:
<223> OTHER INFORMATION: Synthetic peptide

<400> SEQUENCE: 26

Gly Pro Arg Pro Phe Pro Ala Cys
1               5

<210> SEQ ID NO 27
<211> LENGTH: 8
<212> TYPE: PRT
<213> ORGANISM: ARTIFICIAL
<220> FEATURE:
<223> OTHER INFORMATION: Synthetic peptide

<400> SEQUENCE: 27

Gly Pro Arg Pro Pro Glu Arg Cys
1               5

<210> SEQ ID NO 28
<211> LENGTH: 8
<212> TYPE: PRT
<213> ORGANISM: ARTIFICIAL
<220> FEATURE:
<223> OTHER INFORMATION: Synthetic peptide

<400> SEQUENCE: 28

Gly Pro Arg Val Val Glu Arg Cys
1               5

<210> SEQ ID NO 29
<211> LENGTH: 8
<212> TYPE: PRT
<213> ORGANISM: ARTIFICIAL
<220> FEATURE:
<223> OTHER INFORMATION: Synthetic peptide

<400> SEQUENCE: 29

Gly Pro Arg Val Val Ala Ala Cys
1               5

<210> SEQ ID NO 30
<211> LENGTH: 7
<212> TYPE: PRT
<213> ORGANISM: ARTIFICIAL
<220> FEATURE:
<223> OTHER INFORMATION: Synthetic peptide

<400> SEQUENCE: 30

Gly Pro Ser Pro Ala Ala Cys
1               5

<210> SEQ ID NO 31
<211> LENGTH: 6
```

```
<212> TYPE: PRT
<213> ORGANISM: ARTIFICIAL
<220> FEATURE:
<223> OTHER INFORMATION: Synthetic peptide

<400> SEQUENCE: 31

Gly Pro Arg Pro Ala Ala
1               5

<210> SEQ ID NO 32
<211> LENGTH: 5
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 32

Gly Pro Arg Pro Xaa
1               5

<210> SEQ ID NO 33
<211> LENGTH: 5
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 33

Gly Pro Arg Val Xaa
1               5

<210> SEQ ID NO 34
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 34

Gly Pro Arg Pro Xaa Xaa
1               5

<210> SEQ ID NO 35
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 35

Gly Pro Arg Val Xaa Xaa
1               5
```

```
<210> SEQ ID NO 36
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(7)
<223> OTHER INFORMATION: Xaa can be any naturally occurring amino acid

<400> SEQUENCE: 36

Gly Pro Arg Pro Xaa Xaa Xaa
1               5

<210> SEQ ID NO 37
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(7)
<223> OTHER INFORMATION: Xaa can be any naturally occurring amino acid

<400> SEQUENCE: 37

Gly Pro Arg Val Xaa Xaa Xaa
1               5

<210> SEQ ID NO 38
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(8)
<223> OTHER INFORMATION: Xaa can be any naturally occurring amino acid

<400> SEQUENCE: 38

Gly Pro Arg Pro Xaa Xaa Xaa Xaa
1               5

<210> SEQ ID NO 39
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (5)..(8)
<223> OTHER INFORMATION: Xaa can be any naturally occurring amino acid

<400> SEQUENCE: 39

Gly Pro Arg Val Xaa Xaa Xaa Xaa
1               5

<210> SEQ ID NO 40
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (4)..(6)
<223> OTHER INFORMATION: Xaa can be any naturally occurring amino acid
```

```
<400> SEQUENCE: 40

Gly Pro Arg Xaa Xaa Xaa
1               5

<210> SEQ ID NO 41
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (6)..(7)
<223> OTHER INFORMATION: Xaa can be any naturally occurring amino acid

<400> SEQUENCE: 41

Gly Pro Arg Pro Phe Xaa Xaa
1               5

<210> SEQ ID NO 42
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: misc_feature
<222> LOCATION: (6)..(7)
<223> OTHER INFORMATION: Xaa can be any naturally occurring amino acid

<400> SEQUENCE: 42

Gly Pro Arg Val Phe Xaa Xaa
1               5
```

ONE COMPONENT FIBRIN GLUE COMPRISING A POLYMERIZATION INHIBITOR

SEQUENCE LISTING

The instant application contains a Sequence Listing, which is submitted concomitantly with this application via EFS-Web in ASCII format and is hereby incorporated by reference in its entirety. Said ASCII copy, created on Dec. 22, 2013, is named "sequencelisting" and is 8 kilobytes in size.

FIELD OF THE INVENTION

Provided herein is a single component liquid sealant formulation, methods for its preparation, and methods of use thereof for, inter alia, hemostasis, sealing, healing and/or surgery. In particular, disclosed herein is a liquid sealant formulation comprising fibrin monomers and a GPRP peptide. The formulations exhibit stability and extended shelf-life and are useful following blockage, neutralization, dilution of and/or removal of the peptide.

BACKGROUND

Fibrin sealants, also known as fibrin glue, have been in use in the clinic for decades (see, for example, Tabélé, et al. J Pharm Pharmaceut Sci 2012, 15:124-140; Dickneite, G et al. Thrombosis Res 2003, 112:73-82). Oftentimes, fibrin sealants consist of two liquid components, a fibrinogen comprising component and a thrombin comprising component, which are stored frozen due to their inherent instability. Sometimes fibrin sealant products consist of two freeze dried components, which require reconstitution immediately prior to use and delivery by a conjoined syringe or other double-barreled delivery device. Freeze dried formulations are typically stable, but the fibrinogen component is difficult to reconstitute. Upon mixing the two-component solutions, thrombin cleaves fibrinogen thus allowing the latter to generate fibrin polymers.

A fibrin sealant clot is formed by enzymatic reactions involving fibrinogen, thrombin and Factor XIII. Fibrinogen is the precursor protein of the blood clot matrix. It has a molecular weight of ~340,000 Daltons and consists of 3 pairs of non-identical polypeptide chains, Aα, Bβ and γ, linked together by disulfide bonds. Fibrinogen has a trinodular structure: two identical D terminal globular domains and a central E globular domain connected by supercoiled α-helices. Thrombin converts the fibrinogen to fibrin monomers by enzymatic action at a rate determined by the concentration of thrombin.

Factor XIII, an enzyme of the blood coagulation system, typically present in the glue formulation, cross-links and stabilizes the fibrin clot when activated by thrombin and in the presence of calcium. This process bypasses most of the steps of normal coagulation and mimics its last phase. Some manufacturers add anti-proteolytic agents to the fibrin glue formulation (e.g. as described in WO93/05822) or specifically remove the plasminogen in order to stop or delay fibrinolysis (e.g. as described in U.S. Pat. Nos. 5,792,835 and 7,125,569).

Background art includes Laudano and Doolittle (PNAS 75(7):3085-9) and U.S. Pat. Nos. 5,219,328; 5,318,524; 8,367,802; 5,750,657; 6,262,236; 6,268,483; 6,500,427; 5,723,579; 5,478,810; 5,607,858; 6,908,899 and 8,513,380.

SUMMARY OF THE INVENTION

Preparation of a fibrin sealant prior to use is time consuming and cumbersome. The commercialized sealants consist of two components, a fibrinogen comprising component and a thrombin comprising component, which are typically supplied as dry powders or separate frozen liquids. The process for reconstituting the powders is time-consuming because of the limited solubility of the fibrinogen component, and often requires heating. Once reconstituted or thawed, the components are transferred to two separate syringes for immediate use. There are known single component sealants that require cumbersome handling and/or have a short shelf life.

Provided herein are single component, stable sealant formulations comprising fibrin monomers and a GPRP peptide or other reversible fibrin polymerization blocking agent, methods of manufacture and methods of use, which overcome drawbacks of known sealant product formulations, methods of manufacture and/or methods of use.

A reversible fibrin polymerization blocking agent can be an agent of less than about one (1) kD in size. In some embodiments, the agent is a small molecule and/or an isolated peptide, a derivative or salt thereof, which is capable of reversibly binding a fibrin monomer and prevent or delay fibrin polymerization. In some embodiments, the reversible fibrin polymerization blocking agent comprises a small chemical molecule or an isolated peptide. The reversible fibrin polymerization blocking agent may be a low affinity binding agent to fibrin monomers and having no permanent effects on fibrin polymerization. Therefore, typically dilution and/or small molecule exchange will initiate polymerization. The blocking agent herein does not act by lowering pH to an acidic pH.

In one aspect, provided is a liquid sealant formulation comprising fibrin monomers at a concentration of 1 to 13%, (w/v); and a GPRP peptide and/or other reversible fibrin polymerization blocking agent; wherein the blocking agent and/or the GPRP peptide is present in an amount which is greater than about 100 or greater than about 340 molar excess relative to the fibrin monomers; and wherein the liquid formulation is stable for at least 14 days at an ambient temperature selected from the group consisting of about 20, 21, 22, 23, 24, and 25° C.

In one embodiment, the liquid formulation is stable for up to 90 days at an ambient temperature selected from the group consisting of about 20, 21, 22, 23, 24, and 25° C.

In one embodiment, the liquid formulation is stable for a period of time in the range of 14 days and up to 90 days at an ambient temperature selected from the group consisting of about 20, 21, 22, 23, 24, and 25° C.

In one embodiment, the GPRP peptide is present in an amount of about greater than 100 to about 460 or greater than 100 to about 340, or about 340 to about 460 fold molar excess relative to the fibrin monomers.

The term "fibrin monomers" as used herein includes fibrin monomers, dimers and oligomers having a number of fibrin units so that the fibrin is maintained in soluble form in an aqueous liquid solution at an ambient temperature selected from the group consisting of about 20, 21, 22, 23, 24, and 25° C.

In one embodiment, an oligomer contains up to 10 fibrin units.

The term "fibrin polymer" as used herein includes a plurality of fibrin units having a number of fibrin units that limit the solubility of the fibrin in an aqueous liquid solution at an ambient temperature selected from the group consisting of about 20, 21, 22, 23, 24, and 25° C.

In one embodiment, a polymer contains more than 10 fibrin units.

"An ambient temperature" is the temperature in the surrounding environment of the fibrin formulation.

In one embodiment, the formulation is stable for a longer period of time when kept at a lower temperature e.g. 2-8° C. or frozen. After thawing, the formulation can be transferred to a location having an ambient temperature of about 20-25° C. and remain stable for at least 14 days at that temperature. The formulation may also be stable at temperatures other than those specifically disclosed above.

In various embodiments, the fibrin monomers are present at a concentration of 1 to 4% (w/v) or 3.5 to 13% (w/v).

In some embodiments, the formulation further comprises a pharmaceutically acceptable carrier.

The term a "pharmaceutically acceptable carrier" refers to any diluent or a vehicle which is suitable for human or other animal use.

In some embodiments, the formulation is substantially free of added thrombin. "Substantially free" refers to less than about one (1) IU of thrombin per milliliter (U/ml) of formulation.

In some embodiments, the GPRP peptide includes a peptide, derivative or salt thereof comprising the Gly-Pro-Arg-Pro tetrapeptide amino acid sequence.

In some embodiments, the GPRP peptide is a tetrapeptide having amino acid sequence set forth in SEQ ID NO: 1, or a derivative or salt thereof.

In some embodiments, the GPRP peptide is a tetrapeptide consisting of an amino acid sequence set forth in SEQ ID NO: 1, or a derivative or salt thereof.

In various embodiments, the term "GPRP peptide" includes a peptide selected from the group of peptides having an amino acid sequence selected from SEQ ID NO:1-SEQ ID NO:42 (SEQ ID NO:1; SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; SEQ ID NO:40 SEQ ID NO:41; and SEQ ID NO:42) or derivative or salt thereof.

In various embodiments, the GPRP peptide is selected from the group of peptides having an amino acid sequence selected from SEQ ID NO:1 to SEQ ID NO:42 or derivative or salt thereof.

In various embodiments, the GPRP peptide is selected from the group of peptides consisting of an amino acid sequence selected from SEQ ID NO:1 to SEQ ID NO:42 or derivative or salt thereof.

In some embodiments, the GPRP peptide is a GPRP peptide amide.

In some embodiments, the formulation further comprises thrombin-activated Factor XIII. The formulation may further include a calcium chelator. The calcium chelator may be a citrate ion, oxlate ion, EDTA, EGTA or a combination of such calcium chelators. In various embodiments, the calcium chelator is a citrate ion provided, for example, as sodium citrate. Sodium citrate may be present in the formulation at a concentration of about 1 mM to about 50 mM. The formulation may include EDTA and/or EGTA, for example, about 0.1 to about 2.5 mM EDTA and/or EGTA.

In some embodiments, the formulation has a neutral pH, for example, pH of about 6-8, or pH of about 6.5-7.5 or pH of about 6.7-7.2.

In some embodiments the formulation contains a buffer. Typically, a buffer is an ingredient that prevents radical shifts in pH. In one embodiment the buffer is selected from the group consisting of sodium citrate, sodium oxalate, sodium acetate, glycine, arginine and combinations thereof.

The formulation may be used in hemostasis, healing, sealing and/or in surgery, for example in tissue sealing, wound healing, dura healing, suture replacement or anastomosis.

In another aspect, provided herein is a container holding a liquid sealant formulation as disclosed herein. In some embodiments, the container is an ampoule, a vial or a prefilled syringe comprising the formulation. In some embodiments, the formulation or the individual components of the formulation are lyophilized. Provided herein is a container holding a lyophilized formulation that upon reconstitution provides a liquid sealant formulation as disclosed herein.

In another aspect, provided herein is a kit, which includes a container comprising a liquid sealant formulation as disclosed herein, and optionally a small molecule exchange device or G removal device (and optionally instructions for use).

A small molecule exchange device can be any module containing a resin pre-equilibrated with a small molecule permissive for fibrin polymerization. Small molecules within the formulation are exchanged for said polymerization permissive small molecule.

Typically, small molecule exchange is the replacement of at least one small molecule with at least another small molecule. The resin in the column is pre-equilibrated with one or more small molecules(s) that are desired in the final formulation and/or molecules that permit fibrin polymerization. The resin beads are typically porous, the pores being in the range of molecular weights of those molecules which are to be replaced.

In one embodiment, a liquid formulation comprising the fibrin monomers and GPRP peptide is passed through a column that is packed with the porous resin. The fibrin monomers in the formulation will be too large to enter the pores of the resin and will quickly pass through the column. Without being bound by the mechanism, a small molecule e.g. GPRP peptide in the solution will travel a more tortuous path, as they are able to enter and re-exit the pores of the resin, thus greatly slowing their rate of migration through the resin. Without wishing to be bound to theory, the small molecules with which the resin has been pre-equilibrated have a significant head-start, and therefore exit the resin together with the proteins (e.g. fibrin monomers). Thus, the buffer, salts and other small molecules, are exchanged in this step.

In one embodiment before and/or during application of the formulation, the GPRP is diluted with respect to the fibrin monomers and is in a ratio of equal to or lower than 100 such as in the ratio of 1-60, for example 3, 4, 11, 11.3, 17, 22.7, 23, 34, 45, 56.7, or 57.

In another embodiment, the formulation or individual components of the formulation in the kit are lyophilized. Accordingly, the kit comprises a container comprising the fibrin monomers as a powder or a liquid, a container comprising the GPRP peptide as a powder or a liquid and optionally a container comprising a reconstitution liquid such as water, an acetate buffer, or glycine buffer, or arginine buffer at a neutral pH or a citrate buffer at a neutral pH. In one embodiment, the dry fibrin monomers and GPRP peptide powder are provided in the same container.

The formulation in the container or in the kit may further comprise a pharmaceutically acceptable carrier.

In yet another aspect, provided is a method for preparing a sealant at a surface comprising:
a) providing a liquid sealant formulation as disclosed herein; and
b) applying the formulation to the surface under conditions which facilitate fibrin polymerization at the surface.

In some embodiments, the surface is a bleeding or non-bleeding organ/tissue of a subject. A subject includes mammalian animals, including humans, and may be a human patient. In some embodiments, the human patient is a surgery patient.

A "surface" is a position or location where one desires to form the sealant or glue. The surface depends on the use of the sealant. The sealant may be used, for example, in hemostasis, tissue fixation, graft fixation, wound healing and anastomosis. The formulations, methods, and kits disclosed herein can be used internally and externally, for tissue and organ graft fixation, for sealing a surgical wound, in vascular surgery including providing hemostasis and for anastomoses such as arterial, gastrointestinal and tracheal anastomoses.

The surface can be an external surface of the skin that can be seen by unaided vision and a surface of an internal body part which is a part of the internal anatomy of an organism. External surfaces include, but are not limited to, the skin of the face, throat, scalp, chest, back, ears, neck, hand, elbow, hip, knee, and other skin sites. Examples of internal body parts include, but are not limited to, body cavity or anatomical opening that are exposed to the external environment and internal organs such as the nostrils; the lips; the ears; the genital area, including the uterus, vagina and ovaries; the lungs; the anus; the spleen; the liver; and the cardiac muscle. The surface can be a bleeding or a non-bleeding site. The surface can also be a working surface.

In some embodiments, the conditions comprise removing, blocking, neutralizing and/or diluting the GPRP peptide. The GPRP peptide may be removed or diluted by applying the formulation directly to the surface. Alternatively, the GPRP peptide may be removed or diluted by passing the formulation through a small molecule exchange device. Also, it may be removed or diluted by passing the formulation through a size exclusion and/or affinity based device prior to or during application to the surface. Other removal or dilution options include addition of GPRP-complimentary moieties to the device. Complimentary moieties in the device would be essentially an affinity method.

Alternatively or in addition, the GPRP in the formulation could be neutralized and/or blocked by adding a peptide e.g. a complementary moiety of a GPRP peptide or an antibody capable of displacing GPRP bound to the fibrin.

In yet a further aspect provided is a method of healing, sealing and/or reducing blood loss in a subject in need, comprising applying to the subject a therapeutically effective amount of a liquid sealant formulation disclosed herein. The formulation is applied to the subject under conditions which facilitate fibrin polymerization. In some embodiments, the conditions comprise removing, blocking, neutralizing and/or diluting the GPRP peptide.

The term "a therapeutically effective amount" refers to the dose required to prevent, ameliorate and/or treat a disease, disorder or condition. The effective dose can be changed depending on the age and weight of the subject, the disease or condition and its severity and other factors which can be recognized by the skilled in the art.

In another aspect, provided is a liquid sealant formulation as disclosed herein for use in healing, sealing, reducing blood loss and/or surgery.

In yet another aspect, provided herein is a method of manufacturing a liquid sealant formulation as disclosed herein, comprising:
a) providing a component comprising fibrin monomers;
b) providing a GPRP peptide or other reversible fibrin polymerization blocking agent, a derivative or salt thereof;
c) admixing a) and b) in order to obtain the liquid sealant formulation comprising the GPRP in an amount which is greater than 100 or greater than at least 340 fold molar excess relative to the fibrin monomers and fibrin monomer concentration of 1 to 13% (w/v).

In certain embodiment the ratio is of about greater than 100 to about 460 or greater than 100 to about 340, or about 340 to about 460 fold molar excess relative to the fibrin monomers.

The term "admixing" means mixing the components in any order, any combination and/or sub-combination.

Further provided is a liquid sealant formulation obtainable by the method.

The fibrin monomers may be obtained by contacting an aqueous fibrinogen comprising solution with thrombin under conditions that allow cleavage of fibrinogen to fibrin. In such an embodiment, preparation of fibrin monomers are under conditions that fibrin polymerization is inhibited e.g. in the presence of GPRP or other reversible fibrin polymerization blocking agent. In one embodiment fibrin is obtained from fibrinogen under conditions which inhibit polymerization (e.g. by lowering temperature) and GPRP peptide is added later on.

The thrombin may be free in solution or immobilized on beads.

If thrombin is immobilized on beads, for example beads in batch form or in a column and the fibrinogen component is passed through/contacted with the beads, the resulting formulation/component may comprise residual amounts of thrombin. In some embodiments, the formulation is substantially free of thrombin, for example, has less than about one (1) IU/ml of thrombin.

In some embodiments, the formulation/component includes thrombin-activated Factor XIII.

Alternatively, the fibrin monomers in the formulations may be obtained by contacting an aqueous fibrinogen comprising solution with a thrombin-like enzyme under conditions that allow cleavage of fibrinogen to fibrin. Examples of such an enzyme are snake venom enzymes that cleave fibrinopeptide A (FpA) like Batroxobin. In such an embodiment, preparation of fibrin monomers are under conditions that fibrin polymerization is inhibited e.g. in the presence of GPRP or other reversible fibrin polymerization blocking agent.

In some embodiments, the fibrin monomer component/formulation further includes a calcium chelator.

In some embodiments, the method of manufacturing includes a step of drying to provide a dry formulation.

The GPRP peptides and/or the component comprising fibrin monomers can be in powder and/or liquid form.

Further provided is a sealant formulation manufactured using the method provided herein.

The fibrinogen can be prepared from initial blood composition. The blood composition can be whole blood or blood fractions, i.e. a product of whole blood such as plasma. Fibrinogen can be autologous, human including pooled plasma, or of non-human source. It is also possible that the fibrinogen is prepared by recombinant methods or can be chemically modified.

In one embodiment of the invention, the fibrinogen solution is comprised from a biologically active component (BAC) which is a solution of proteins derived from blood plasma which can further comprise anti fibrinolytic agents such as tranexamic acid and/or stabilizers such as arginine, lysine, their pharmaceutically acceptable salts, or mixtures thereof. BAC can be derived from cryoprecipitate, in particular concentrated cryoprecipitate.

The term "cryoprecipitate" refers to a blood component which is obtained from frozen plasma prepared from whole blood. A cryoprecipitate can be obtained when frozen plasma is thawed in the cold, typically at a temperature of 0-4° C., resulting in the formation of precipitate that contains fibrinogen and factor XIII. The precipitate can be collected, for example by centrifugation and dissolved in a suitable buffer such as a buffer containing 120 mM sodium chloride, 1 mM calcium chloride, 10 mM trisodium citrate, 120 mM glycine, 95 mM arginine hydrochloride. The solution of BAC can comprise additional factors such as for example factor VIII, fibronectin, von Willebrand factor (vWF), vitronectin, etc. for example as described in U.S. Pat. No. 6,121,232 and WO9833533. The composition of BAC can comprise stabilizers such as tranexamic acid and arginine hydrochloride. The amount of tranexamic acid in the solution of BAC can be from about 80 to about 110 mg/ml.

In another embodiment, the concentration of plasminogen and plasmin in the BAC composition is lowered to equal or less than 15 μg/ml like for example 5 μg/ml or less plasminogen e.g. using a method as described in U.S. Pat. No. 7,125,569, EP 1,390,485 and WO02095019. In another embodiment of the invention, when the concentration of plasminogen and plasmin in the BAC composition is lowered, the composition does not contain tranexamic acid or aprotinin.

The fibrinogen solution may be the BAC2 component (from EVICEL®) or any other fibrinogen containing solution, such as purified recombinant fibrinogen or cryoprecipitate produced from human plasma.

In one embodiment the formulation is a fully dissolved solution e.g. a solution whose solute and solvent constitute only one phase, e.g. a liquid phase.

These and other aspects and embodiments of the invention will become evident upon reference to the following detailed description of the invention and the figures.

DETAILED DESCRIPTION OF THE INVENTION

Figure 1:
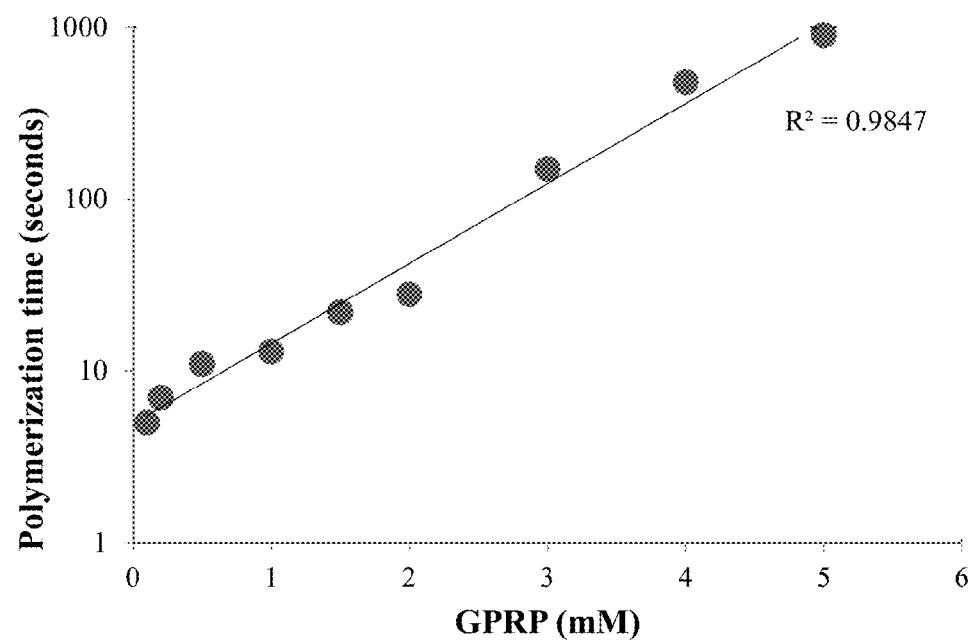
FIG. 1 is a graph showing the effect of GPRP peptide concentration on fibrin polymerization time at a fixed fibrin concentration.

The present disclosure is based, in part, upon the finding of a stable sealant formulation which includes fibrin monomers and a GPRP peptide at a certain concentration.

Provided herein are liquid sealant formulations comprising fibrin monomers and a GPRP peptide at a certain molar ratio, which overcome the deficiencies of the currently available sealant formulations. Further provided herein are methods of manufacturing and methods of using the formulations.

Provided herein is a liquid sealant formulation comprising a) fibrin monomers; and b) a GPRP peptide or other reversible fibrin polymerization blocking agent. The fibrin monomers are present at a concentration of about 1% to about 13% (weight per volume (w/v)). In one embodiment, the GPRP peptide has the amino acid sequence Gly-Pro-Arg-Pro (GPRP; SEQ ID NO:1), a derivative or salt thereof and is present in an amount which is greater than 100 fold molar excess relative to the fibrin monomers, greater than or equal to about 340 fold molar excess or about 340 to about 460 fold molar excess relative to the fibrin monomers.

In another embodiment, the GPRP peptide comprises the amino acid sequence Gly-Pro-Arg-Pro (SEQ ID NO: 1) or Gly-Pro-Arg-Val (SEQ ID NO: 23).

In various embodiments, the GPRP peptide is selected from the group of peptides having an amino acid sequence selected from SEQ ID NO:2-SEQ ID NO:42.

Stability can be determined by observing minimal or absence of spontaneous polymerization or clotting in the formulation e.g. the formulation does not show or have spontaneous polymerization or clotting in the presence of GPRP peptide for up to 14 days, and retains its clotting activity level upon removal, dilution, blockage and/or neutralization of GPRP to a molar excess of equal to or less than 100. The clotting activity level or capability of the formulation to form a sealant can be determined in-vitro and/or in-vivo using clotting methods known in the art. Stability can also be determined by measuring and observing the presence of minimal or absence of fibrin polymers or clot in the shelf-ready liquid formulation.

In use, the GPRP effect can be reduced e.g. by dilution to a concentration according to an intended use. For hemostasis it will be of advantage to obtain clotting times which are less than one minute. In one embodiment, the GPRP concentration in the formulation is diluted to a molar excess of equal or less than 100 fold or to a molar excess of equal or less than 34 fold.

For graft fixation it will be of advantage to obtain clotting times which are approximately 15 minutes. In one embodiment, the GPRP concentration in the formulation is diluted to a molar excess of equal to or less than 100 fold or to a molar excess of equal to or less than 56 fold.

The terms "stable" and "stability" when referring to the liquid sealant formulation, mean an absence of fibrin polymerization/fibrin clot in the formulation before its application to a surface. The formulations disclosed herein are stable at an ambient temperature as defined above for at least 14 (fourteen) days.

Fibrin polymerization or clotting can be measured, for example, by measuring migration length on a slanted surface (or drop test model) or by any other method known in the art. Full polymerization can be assessed by cessation of flow of the liquid formulation e.g. upon inversion. Rapid polymerization can be measured using a Stat4 clotting analyzer Stago Diagnostics or similar coagulometer.

For long-term storage e.g. 1 year or more at 2-8° C., the formulation, comprising the fibrin monomers and the GPRP peptide may be aliquoted into sterile vials, ampoules, or other containers, which are then sealed. In one embodiment, a seal that permits removal of the formulation with a syringe through the seal is used. The container can be labeled according to standard practice in the pharmaceutical or medical device field.

In use, the liquid sealant formulation can be applied directly from the container, can be passed through a small molecule exchange device, or through a GPRP removal device (e.g. an affinity device having a GPRP-complimentary moiety); although the method of use will be determined by the user (e.g. medical practitioner such as a physician, nurse, medic) i.e. according to the needs of the individual patient and on the severity of bleeding or condition.

As used herein, the indefinite articles "a" and "an" mean "at least one" or "one or more" unless the context clearly dictates otherwise.

As used herein, the terms "comprising", "including", "having" and grammatical variants thereof are to be taken as specifying the stated features, steps or components but do not preclude the addition of one or more additional features, steps, components or groups thereof.

When a numerical value is preceded by the term "about", the term "about" is intended to indicate +/−10%.

As used herein, the term "peptide" is used broadly to mean an isolated compound of about 4 to about 50 consecutive amino acids, or analogs of amino acids. Included within the definition of peptide are, for example, peptides containing one or more analogs of an amino acid (including, for example, synthetic amino acids, peptoids, etc.), peptides with substituted linkages, peptide salts, as well as other modifications known in the art, both naturally occurring and non-naturally occurring (e.g., synthetic). Thus, synthetic peptides, cyclized, branched peptides and the like, are included within the definition.

The term "peptides" also includes derivatives of the amino acid sequences of the invention having one or more substitution, addition and/or deletion, including one or more non-naturally occurring amino acid. Preferably, derivatives exhibit at least about 50% identity to the reference sequence, preferably at least about 70% identity, more preferably at least about 75%, 80%, 85%, 90%, 91%, 92%, 93%, 94%, 95%, 96%, 97%, 98%, 99% or 100% sequence identity to the reference sequence described herein. Peptide derivatives can include modifications to the native sequence, such as deletions, additions and substitutions (generally conservative in nature), so long as the peptide maintains the desired activity e.g. reversibly inhibiting fibrin polymerization.

These modifications may be deliberate, as through site-directed mutagenesis, or may be accidental, such as through synthesis or mutations of hosts that produce the proteins or errors due to PCR amplification. Further encompassed herein are pharmaceutically acceptable salts of peptides and their derivatives of such salts.

Reversible inhibitor relates to a low affinity of the inhibitor (e.g. GPRP peptide) to fibrin monomer and having no permanent effects on fibrin polymerization or fibrin clot. Therefore, typically dilution, removal and/or small molecule exchange will remove the inhibitory effect.

The term "reversible polymerization inhibitor" is interchangeable herein with the term "reversible fibrin polymerization blocking agent".

By "GPRP peptide" it is meant a peptide of four or more consecutive amino acid sequence set forth in SEQ ID NO: 1, specifically the sequence Gly-Pro-Arg-Pro. A GPRP peptide may comprise a tetramer (GPRP, SEQ ID NO: 1), a derivative or analog thereof. A GPRP peptide may be 4 to 12 amino acid residues in length, or 4 to 8 preferably 4, 5, 6, 7 or 8 amino acids in length.

Without wishing to be bound to theory, a GPRP peptide is capable of binding to a fibrin monomer, thereby blocking association and polymerization of fibrin monomers. The GPRP peptide may comprise, for example, a GPRP peptide amide (amide at C terminus) disclosed in U.S. Pat. Nos. 5,478,810 and 5,607,858, incorporated by reference, having formula GPRP—X—N($R_1R_2$) wherein G is the amino acid glycine, P is the amino acid L-proline, R is the amino acid L-arginine, X is a proteinogenous amino acid other than proline or is a dipeptide including proline, N is nitrogen and $R_1$ and $R_2$ are identical or different and are hydrogen or a lower alkyl chain having up to 4 carbon atoms. Other GPRP peptides include peptides termed "fibrin knob peptides" disclosed in U.S. Pat. No. 8,513,380 such as a peptide having amino acid sequence GPRP (SEQ ID NO:1), GPRV (SEQ ID NO:2), or GHRP (SEQ ID NO:3). The GPRP peptide can have the amino acid sequence GPRPX (SEQ ID NO:32), GPRVX (SEQ ID NO:33), GPRPXX (SEQ ID NO:34), GPRVXX (SEQ ID NO:35), GPRPXXX (SEQ ID NO:36), GPRVXXX (SEQ ID NO:37), GPRPXXXX (SEQ ID NO:38), or GPRVXXXX (SEQ ID NO:39), or GPRXXX (SEQ ID NO:40) where X is any amino acid.

The peptide can also have a C-terminal amino acid, such as for example cysteine or lysine, that enables subsequent chemical reactions with other agents to produce C-terminal conjugates. Therefore, in some embodiments, the C-terminal amino acid of the peptide is a cysteine. Therefore, in some embodiments, the C-terminal amino acid of the peptide is a lysine. For example, the GPRP peptide can have the amino acid sequence GPRPAAC (SEQ ID NO: 25), GPRPFPAC (SEQ ID NO: 26), GPRPPERC (SEQ ID NO: 27), GPRVVERC (SEQ ID NO: 28), GPRVVAAC (SEQ ID NO: 29), or GPSPAAC (SEQ ID NO: 30).

Any of the peptide sequences set forth in SEQ ID NOS: 1-42 may be a peptide amide e.g. as disclosed in the above referenced patents.

Amino acids and peptide sequences are commonly abbreviated as shown below, in Table A.

TABLE A

| | | | Abbreviation, systematicnames and formulae of common amino acids | |
|---|---|---|---|---|
| | Symbols/ abbreviations | | | |
| Name | 3 ltr | 1 ltr | Systematic name | Formula |
| Alanine | Ala | A | 2-Aminopropanoic acid | $CH_3$—$CH(NH_2)$—COOH |
| Arginine | Arg | R | 2-Amino-5-guanidinopentanoic acid | $H_2N$—C(=NH)—NH—$[CH_2]_3$—$CH(NH_2)$—COOH |

TABLE A-continued

Abbreviation, systematic names and formulae of common amino acids

| Name | 3 ltr | 1 ltr | Systematic name | Formula |
|---|---|---|---|---|
| Asparagine | Asn | N | 2-Amino-3-carbamoylpropanoic acid | $H_2N-CO-CH_2-CH(NH_2)-COOH$ |
| Aspartic acid | Asp | D | 2-Aminobutanedioic acid | $HOOC-CH_2-CH(NH_2)-COOH$ |
| Cysteine | Cys | C | 2-Amino-3-mercaptopropanoic acid | $HS-CH_2-CH(NH_2)-COOH$ |
| Glutamine | Gln | Q | 2-Amino-4-carbamoylbutanoic acid | $H_2N-CO-[CH_2]_2-CH(NH_2)-COOH$ |
| Glutamic acid | Glu | E | 2-Aminopentanedioic acid | $HOOC-[CH_2]_2-CH(NH_2)-COOH$ |
| Glycine | Gly | G | Aminoethanoic acid | $CH_2(NH_2)-COOH$ |
| Histidine | His | H | 2-Amino-3-(1H-imidazol-4-yl)propanoic acid | $C_6H_9N_3O_2$ |
| Isoleucine | Ile | I | 2-Amino-3-methylpentanoic | $C_2H_5-CH(CH_3)-CH(NH_2)-COOH$ |
| Leucine | Leu | L | 2-Amino-4-methylpentanoic acid | $(CH_3)_2CH-CH_2-CH(NH_2)-COOH$ |
| Lysine | Lys | K | 2,6-Diaminohexanoic acid | $H_2N-[CH_2]_4-CH(NH_2)-COOH$ |
| Methionine | Met | M | 2-Amino-4-(methylthio)butanoic | $CH_3-S-[CH_2]_2-CH(NH_2)-COOH$ |
| Phenylalanine | Phe | F | 2-Amino-3-phenylpropanoic acid | $C_6H_5-CH_2-CH(NH_2)-COOH$ |
| Proline | Pro | P | Pyrrolidine-2-carboxylic acid | $C_5H_9NO_2$ |
| Serine | Ser | S | 2-Amino-3-hydroxypropanoic acid | $HO-CH_2-CH(NH_2)-COOH$ |
| Threonine | Thr | T | 2-Amino-3-hydroxybutanoic acid | $CH_3-CH(OH)-CH(NH_2)-COOH$ |
| Tryptophan | Trp | W | 2-Amino-3-(1H-indol-3-yl)-propanoic acid | $C_{11}H_{12}N_2O_2$ |
| Tyrosine | Tyr | Y | 2-Amino-3-(4-hydroxy phenyl)-propanoic acid | $HO-p-Ph-CH_2-CH(NH_2)-COOH$ |
| Valine | Val | V | 2-Amino-3-methylbutanoic acid | $(CH_3)_2CH-CH(NH_2)-COOH$ |

In one embodiment, an amino acid analog sequence is used whereby at least one amino acid in the isolated peptide is substituted with an analog or bio-similar amino-acid (conservative substitution), as known in the art. The amino acids can be in L form, D form, or their derivatives (e.g. pseudo amino acid, functionalized amino acid (e.g. fluorinated amino acid . . . etc.), beta amino acid, gamma amino acid . . . etc.).

One skilled in the art will recognize that the peptides disclosed herein may be synthesized as derivatives of the peptides, including "peptide mimetics". A peptide mimetic or "peptidomimetic" is a molecule that is not completely peptidic in nature, yet mimics the biological activity of the peptide upon which it is structurally based. Such peptidomimetics include peptide-like molecules containing non-naturally occurring amino acids. A peptidomimetic can include one or more amino acid analogs and can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; imide bond; ketomethylene or fluoroketomethylene bond or another amide isostere. The terms also include molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al. (2000) Chem Biol. 7(7):463-473; and Simon et al. (1992) Proc. Natl. Acad. Sci. USA 89(20):9367-9371 for description of peptoids). One skilled in the art understands that these and other peptidomimetics are encompassed within the meaning of the term "peptidomimetic" as used herein.

The amino acid sequence of a peptide is written according to the conventional notation, with an amino group ($NH_2$) at the N-terminal appearing on the left hand of the sequence and carboxyl group (COOH) at the C-terminal appearing on the right hand thereof.

The peptides disclosed herein may form a physiologically acceptable salt by conventional salt formation reaction. Such salts can include salts with inorganic acids such as hydrochloric acid, sulfuric acid and phosphoric acid; salts with organic acids such as lactic acid, tartaric acid, maleic acid, fumaric acid, oxalic acid, malic acid, citric acid, oleic acid and palmitic acid; salts with hydroxides and carbonates of alkali metals and alkali earth metals such as sodium, potassium, calcium and aluminum; and salts with amines such as triethylamine, benzylamine, diethanolamine, t-butylamine, dicyclohexylamine and arginine.

Both inter- and intra-chain disulfide bonds may be formed and the peptide forms resulting from the formation of such disulfide bonds are encompassed by the present invention.

In one embodiment, the peptides disclosed herein are chemically synthesized. In other embodiments, the peptides disclosed herein are produced in-vivo or ex-vivo by expression of recombinant DNA in prokaryotic or eukaryotic host cells.

In some embodiments, the GPRP peptides reversibly bind the C-terminal region of the fibrin and fibrinogen chain. It is to be understood that a preferential interaction does not necessarily require interaction between specific amino acid residues and/or motifs of each peptide.

The term "substantially free of thrombin" or "thrombin-free" relates to a component or formulation having no more than about 1 (one) unit of thrombin per milliliter (ml) formulation.

The term "an effective amount" refers to the amount of a component or formulation disclosed herein required to form a sealant e.g. to cover an injured surface, to reduce bleeding, to increase healing, to ameliorate an undesired condition etc.

The "pharmaceutically acceptable" or "pharmacologically acceptable" carriers, solvents, diluents, excipients, and vehicles generally refer to inert, non-toxic solid or liquid fillers, diluents or encapsulating material not reacting with the active ingredients of the compositions disclosed herein. Acceptable excipients include, without limitation, saline; acetic acid or acetate; and sodium chloride ions; mannitol; albumin; or combination thereof.

Peptides disclosed herein are synthesized according to methods known in the art, including, but not limited to synthetic (e.g. synthesizing the peptide chemically from individual amino acids) and recombinant methods (e.g. synthesizing DNA encoding the peptide and using the DNA to produce recombinant peptide).

Chemical synthesis of the peptide: a peptide disclosed herein and DNA encoding the peptide may be chemically synthesized by methods known in the art. Suitable methods for synthesizing the peptide are described by Stuart and Young (1984), "Solid Phase Peptide Synthesis," Solid Phase Peptide Synthesis, Methods Enzymol., Second Edition, Pierce Chemical Company, 289, Academic Press, Inc., NY (1997). For example, a solid phase synthesis method or a liquid phase synthesis method may be used. The solid phase synthesis is usually carried out by protecting amino groups with appropriate protecting groups. For example, either Boc (tert-butoxycarbonyl) or Fmoc (9-fluorenylmethyloxycarbonyl), or a combination thereof may be used. In one example, a peptide disclosed herein is synthesized by following the steps: 1) an amino acid residue corresponding to the C-terminal of the peptide to be produced is bonded to a solid phase material insoluble to a reaction solvent via an a-COOH group of the amino acid or such solid phase material is purchased; 2) in the direction towards the N-terminal of the peptide, a corresponding amino acid or peptide fragment is bonded by condensation to the amino acid of step 1) after protecting other functional groups such as an a-amino group of the corresponding amino acid or peptide fragment other than an a-COOH group; 3) a protecting group of an amino group forming a peptide bond such as an a-amino group is removed from the bonded amino acid or peptide fragment; 4) steps 2) and 3) are repeated to elongate a peptide chain in order to form a peptide chain corresponding to the desired peptide; 5) detach the produced peptide chain from the solid phase material and remove the protecting groups from the protected functional groups; and 6) purify the peptide, thereby to obtain the desired peptide.

Solid phase materials, as well as solvents and a condensing agents, are well known in the art.

Chemical synthesis and expression of DNA: The DNA encoding a peptide disclosed herein may be replicated and used to express recombinant peptide following insertion into a wide variety of host cells in a wide variety of cloning and expression vectors. The host may be prokaryotic or eukaryotic. The DNA may be chemically synthesized. Suitable methods for synthesizing DNA and cloning vectors (e.g. for use in mammalian, insect or plant cells, bacteria, phage and yeast) are available. The recombinant peptide, which can be expressed in the form of a fusion protein, is purified by methods known in the art.

While the following examples demonstrate certain embodiments of the invention, they are not to be interpreted as limiting the scope of the invention, but rather as contributing to a complete description of the invention.

EXAMPLES

Example 1

Effect of GPRP Peptide Concentration on Fibrin Polymerization Time

To evaluate the effect of the presence of a peptide and its concentration on fibrin monomers polymerization rate, a mixture of GPRP peptide:fibrin monomers was incubated and the time until a clot was formed was measured.

A mixture of GPRP peptide:fibrin monomers was prepared as follows:

GPRP peptide (Gly-Pro-Arg-Pro; custom made by Sigma; the peptide was supplied in lyophilized form (250 mg) and dissolved in 100 mM tri-Sodium Citrate dihydrate; pH=7 creating 1 M GPRP) was added to a fibrinogen solution (BAC2 solution as in EVICEL® Fibrin Sealant). The peptide final concentration in the solution is listed in Table 1 below. Fibrinogen final concentration used was 1%, 1.5%, 3%, 3.5%. A BAC2 solution [fibrinogen component of EVICEL®] containing 7% clottable fibrinogen was diluted in 20 mM sodium acetate (NaAcetate) buffer, pH 7.0 to obtain the final listed concentrations.

To form fibrin, thrombin (as in EVICEL® Fibrin Sealant) was added to the fibrinogen solution at a final concentration of 10 IU/ml or 100 IU/ml and then the time to clot was recorded. Clotting was assessed by cessation of flow when inverting the tube.

Table 1 provides an outline of the clotting time per fibrin and peptide final concentrations.

The fibrin monomer concentration was estimated as being equal to the fibrinogen concentration.

TABLE 1 clotting time as a function of fibrin and peptide concentration.

| GPRP concentration | Time to clot | Fold (GPRP:fibrin) |
|---|---|---|
| SHORT TERM EXPERIMENTS 1% fibrin monomers | | |
| 0.1 mM | Immediate | 3.4 |
| 1 mM | <5 minutes | 34 |
| 5 mM | 4 hours | 170 |
| 10 mM | 7-8 days | 340 |
| 3% fibrin monomers | | |
| 0.1 mM | 5 seconds | 1.1 |
| 0.2 mM | 7 seconds | 2.3 |
| 0.5 mM | 11 seconds | 5.7 |
| 1 mM | 13 seconds | 11.3 |
| 1.5 mM | 22 seconds | 17 |
| 2 mM | 28 seconds | 22.7 |
| 3 mM | 2.5 minutes | 34 |
| 4 mM | 8 minutes | 45 |
| 5 mM | 15 minutes | 56.7 |
| LONG TERM EXPERIMENTS 1.5% fibrin monomers | | |
| 20 mM | No clotting (>2 weeks) | 453 |
| 3.5% fibrin monomers | | |
| 40 mM | No clotting (>2 weeks) | 389 |

Results of Short Term Experiments:

In general, as the concentration of GPRP peptide was lowered, the fibrin monomers progressively polymerized at a faster rate. For example, 1% fibrin and 0.1 mM GPRP (~3.4:1 molar ratio of GPRP:fibrin), a fibrin clot was formed immediately, at 1% fibrin and 1 mM GPRP (~34:1 molar ratio), a clot formed in less than 5 minutes. At 1% fibrin and 5 mM GPRP (~170:1), the solution was stable as a liquid for 4 hours, and at 1% fibrin and 10 mM GPRP (~340:1), the solution was stable as a liquid for approximately 7-8 days, but did polymerize to form a solid after that.

Results of Long Term Experiments:

At a fibrin concentration of 1.5% and 20 mM GPRP (~453:1), or at 3.5% fibrin and 40 mM GPRP (~389:1), the solution was stable and did not form a clot even after 2 weeks at room temperature.

These experiments show that a molar ratio of 340:1 (GPRP:fibrin) advantageously resulted in stabilization of the liquid solution for about 7-8 days.

Similar results were observed with the two thrombin concentrations used.

Without wishing to be bound to theory, this result indicates that most or all of the fibrinogen was cleaved by the thrombin and the differences in clotting time were related to the GPRP concentrations relative to fibrin.

The relationship between polymerization time and GPRP:fibrin molar ratio is also shown in FIG. 1.

In this experiment, a fixed (3%) fibrin concentration and increasing amounts of GPRP (0.1 mM, 0.2 mM, 0.5 mM, 1 mM, 1.5 mM, 2 mM, 3 mM, 4 mM, and 5 mM) were used to delay polymerization. All of these (having a ratio of at most 57:1) are below the minimal ratio required for long term stabilization of fibrin monomers. The GPRP:fibrin solution was prepared as described above (by adding a GPRP peptide into a fibrinogen solution and adding thrombin into the GPRP:fibrinogen mix). Next, the time to clotting was recorded as above.

FIG. 1 shows that there is a logarithmic correlation between the fibrin polymerization rate and the molar ratio of GPRP peptide to fibrin.

This indicates that the rate of fibrin clot formation can be controlled by adjusting the concentration of the GPRP peptide within the solution and that dilution of the GPRP peptide by even a small amount would affect fibrin polymerization rate.

Furthermore, the defined correlation allows, in some embodiments, the control of the rate of polymerization by the control of the final GPRP peptide concentration after application (e.g. via a small molecule exchange device).

Example 2

Fibrin Clot Formation from a Solution Comprising Fibrin and GPRP Using a Small Molecule Exchange Device The following example aims to show that initiation and/or acceleration of fibrin clot formation can be achieved by using a small molecule exchange device to dilute or remove the GPRP peptide from the solution.

A mixture containing a fibrin concentration of approximately 3.8%, and GPRP peptide concentration of 41 mM GPRP peptide (molar ratio of ~366:1) was prepared as described above (by adding a GPRP peptide into a 3.8% fibrinogen solution and adding thrombin to cleave the fibrinogen into fibrin). This molar ratio was found to be sufficient to maintain the formulation stable.

A commercial small molecule exchange device (GE PD-10 spin columns; Product code: 17-0851-01, GE Healthcare) was used according to the standard spin protocol provided with the device, to remove/dilute the GPRP peptide from the GPRP:fibrin monomer formulation. The exchange device was pre-equilibrated with a buffer including 20 mM sodium acetate pH 7.0; 25 mM calcium chloride. 2.5 ml solution was subjected to the buffer exchange procedure and fibrin clot formation was assessed by inverting the tube containing the buffer-exchanged mixture.

Figure 2A:
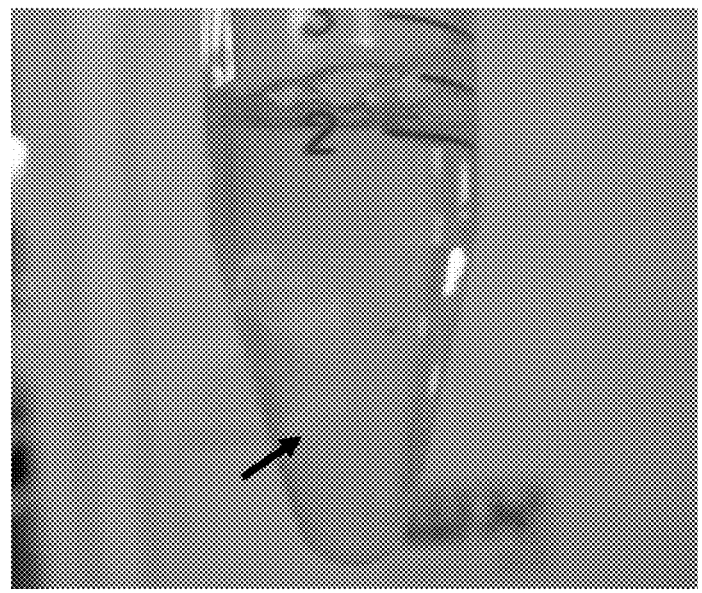
FIG. 2A shows a liquid formulation comprising GPRP peptide and fibrin.
Figure 2B:
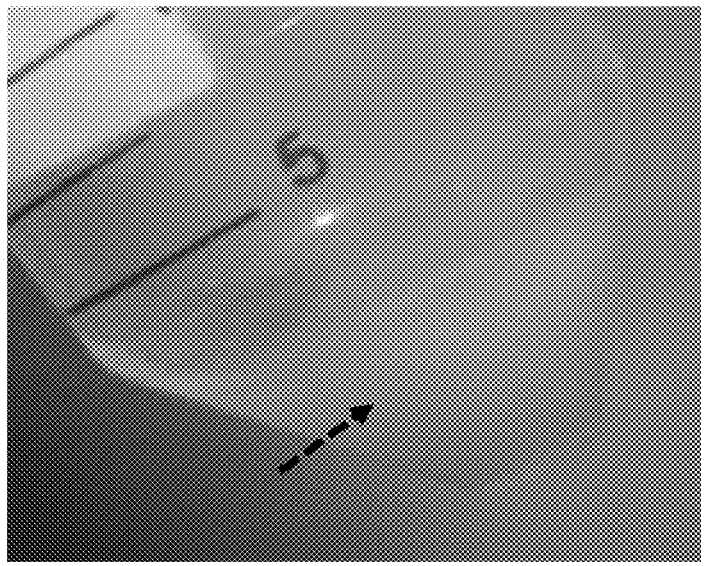
FIG. 2B shows that fibrin polymerization occurred after removal of the GPRP peptide. In this embodiment GPRP peptide was removed by subjecting the formulation to a small molecule exchange device.

The small molecule-exchanged formulation rapidly clotted (FIG. 2B) whereas the solution which was not subjected to the buffer exchange procedure, remained in liquid form (FIG. 2A).

Although various embodiments have been described herein, many modifications and variations to those embodiments may be implemented. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference.

Citation or identification of any reference in this application shall not be construed as an admission that such reference is available as prior art to the invention.

Section headings are used herein to ease understanding of the specification and should not be construed as necessarily limiting.

The invention claimed is:

1. A liquid sealant formulation comprising fibrin monomers at a concentration of 1 to 13% (w/v) and a GPRP peptide for reversible blocking fibrin polymerization wherein the GPRP peptide is present in the formulation in an amount which is greater than 100-fold molar excess relative to the fibrin monomers; and wherein the liquid formulation is stable for at least 14 days at an ambient temperature selected from the group consisting of about 20, 21, 22, 23, 24, and 25° C.

2. The formulation of claim 1, wherein the GPRP peptide is present in an amount greater than about 340-fold molar excess relative to the fibrin monomers.

3. The formulation of claim 1, wherein the GPRP peptide is present in an amount greater than about 340- to 460-fold molar excess relative to the fibrin monomers.

4. The formulation of claim 1, wherein the formulation is substantially free of added thrombin.

5. The formulation of claim 1, further comprising thrombin-activated Factor XIII.

6. The formulation of claim 1, further comprising a calcium chelator.

7. The formulation of claim 6, wherein the calcium chelator is a citrate ion.

8. The formulation of claim 7, wherein the citrate ion is provided by sodium citrate.

9. The formulation of claim 8, comprising from about 1 mM to about 50 mM sodium citrate.

10. The formulation of claim 1, wherein the formulation has a neutral pH.

11. The formulation of claim 1, for use in hemostasis, sealing, healing and/or in surgery.

12. A container comprising the formulation of claim 1.

13. A kit comprising the container of claim 12, and optionally instructions for use.

14. The liquid sealant formulation of claim 1, wherein the GPRP peptide is selected from the group consisting of a sequence set forth in SEQ ID NO:1-SEQ ID NO:42 (SEQ ID NO:1; SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; SEQ ID NO:40; SEQ ID NO:41; and SEQ ID NO:42), and combinations thereof.

* * * * *